United States Patent
Ichino et al.

(10) Patent No.: US 8,012,321 B2
(45) Date of Patent: Sep. 6, 2011

(54) BIOSENSOR CHIP, BIOSENSOR SYSTEM AND MEASURING INSTRUMENT THEREOF

(75) Inventors: Moriyasu Ichino, Osaka (JP); Toshifumi Hosoya, Osaka (JP); Shingo Kaimori, Osaka (JP); Takahiko Kitamura, Osaka (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 289 days.

(21) Appl. No.: 12/280,721

(22) PCT Filed: Feb. 27, 2007

(86) PCT No.: PCT/JP2007/053678
§ 371 (c)(1),
(2), (4) Date: Oct. 8, 2008

(87) PCT Pub. No.: WO2007/102347
PCT Pub. Date: Sep. 13, 2007

(65) Prior Publication Data
US 2009/0255810 A1 Oct. 15, 2009

(30) Foreign Application Priority Data
Feb. 27, 2006 (JP) .............. P.2006-050607
Feb. 27, 2006 (JP) .............. P.2006-050608

(51) Int. Cl.
*G01N 27/327* (2006.01)
(52) U.S. Cl. ............... 204/403.02; 204/403.01
(58) Field of Classification Search ........ 204/403.01–403.15; 205/777.5, 205/778, 792
See application file for complete search history.

(56) References Cited

U.S. PATENT DOCUMENTS

| | | | |
|---|---|---|---|
| 4,999,582 A | 3/1991 | Parks et al. | |
| 5,352,351 A | 10/1994 | White et al. | |
| 5,438,271 A | 8/1995 | White et al. | |
| 5,651,869 A * | 7/1997 | Yoshioka et al. | 204/403.12 |
| 5,804,047 A | 9/1998 | Karube et al. | |
| 6,071,391 A | 6/2000 | Gotoh et al. | |
| 6,156,173 A | 12/2000 | Gotoh et al. | |
| 6,503,381 B1 | 1/2003 | Gotoh et al. | |
| 2003/0102213 A1 | 6/2003 | Gotoh et al. | |
| 2003/0150724 A1* | 8/2003 | Kawanaka et al. | 204/403.02 |
| 2005/0258052 A1 | 11/2005 | Gotoh et al. | |

(Continued)

FOREIGN PATENT DOCUMENTS

JP 5-503158 A 5/1993

(Continued)

OTHER PUBLICATIONS

English language Abstract of JP 2002-257782 A.

*Primary Examiner* — Alex Noguerola
(74) *Attorney, Agent, or Firm* — Greenblum & Bernstein, P.L.C.

(57) ABSTRACT

In a biosensor system and its measuring instrument which determine that a biosensor chip has been inserted and measure biological information on a biological material supplied to the biosensor chip, the size of the biosensor chip is made small, the reliability of the measuring instrument is improved, and the product life becomes long. In addition, a measurement error of the biological information is suppressed in measuring the biological information by inserting a biosensor chip, which has a sensor electrode formed of an electrode member with an electric resistance value higher than a conductive metal, into the measuring instrument.

21 Claims, 5 Drawing Sheets

U.S. PATENT DOCUMENTS

| | | |
|---|---|---|
| 2007/0000776 A1 | 1/2007 | Karube et al. |
| 2007/0068808 A1 * | 3/2007 | Lee .................... 204/403.01 |

FOREIGN PATENT DOCUMENTS

| | | |
|---|---|---|
| JP | 6-090754 A | 4/1994 |
| JP | 8-502589 A | 3/1996 |
| JP | 8-504953 A | 5/1996 |
| JP | 9-159643 A | 6/1997 |
| JP | 11-108879 A | 4/1999 |
| JP | 2002-257782 A | 9/2002 |
| JP | 2005-233917 A | 9/2005 |
| WO | 91/09316 | 6/1991 |
| WO | 94/29705 | 12/1994 |
| WO | 94/29706 | 12/1994 |
| WO | 2005/010519 | 2/2005 |

* cited by examiner

BIOSENSOR CHIP, BIOSENSOR SYSTEM AND MEASURING INSTRUMENT THEREOF

This application just a 371 of PCT/JP2007/053678, filed Feb. 27, 2007, which claims priority from Japanese application JP 2006-050607, filed Feb. 27, 2006, and Japanese application JP 2006-050, filed Feb. 27, 2006.

TECHNICAL FIELD

The present invention relates to a biosensor chip, a biosensor system which measures biological information on a biological material supplied to the biosensor chip, and a measuring instrument thereof.

RELATED ART

A study of bioelectronics for applying a biological function to an electronics field has been progressing. A biosensor chip in this bioelectronics field is a device which uses an excellent molecule recognition function that a living body has, and is promising since it allows chemical substances to be measured quickly and easily. This biosensor chip is applied as a sensor for microsample measurement. For example, the biosensor chip is used as a disposable one for home medical checkup (self-care) that checks and prevents diabetes by measuring a blood sugar level or a urine sugar level or industrially used for sampling quality inspection of the goods on a production line, which has a wide field of application.

In a specific example of measurement, a sample containing a material to be measured is taken out and dropped onto a reaction portion, reduction product generated by enzyme reaction, for example, is oxidized, and a value of an element current by the oxidation is taken out and detected. A measurement value equivalent to the element current value is calculated referring to a data table and is output and displayed (refer to Patent Document 1).

As a measuring instrument which measures such an element current value, one in which a sensor insertion determining circuit is provided as a determining means for recognizing whether or not a sensor chip is inserted into the device body and is in a measurable state and which is configured to measure a measurement value of an element current value of a material to be measured after detecting that the sensor chip has been inserted is proposed. The configuration of a biosensor device capable of detecting that the sensor chip has been inserted is shown in FIG. 9.

Figure 9:
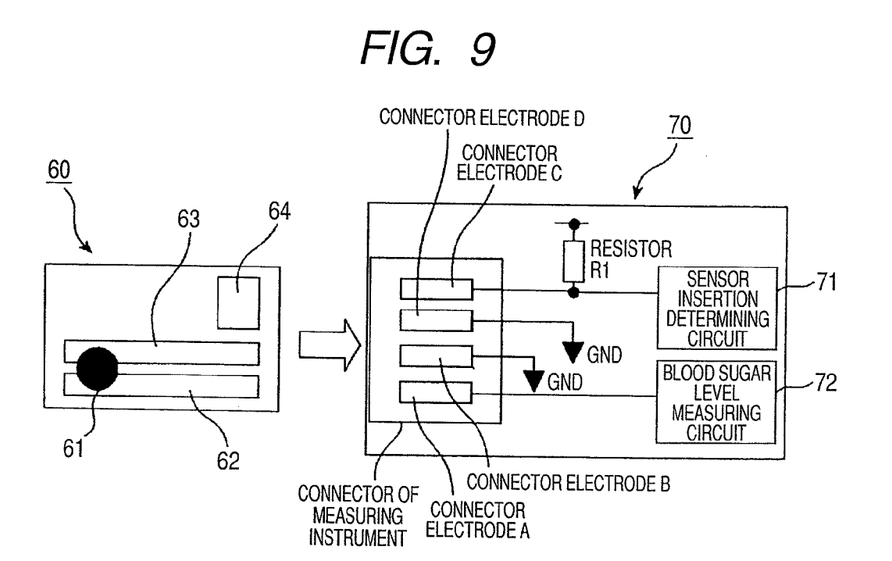
FIG. 9 is a view illustrating the configuration of main parts of known measuring instrument and biosensor chip.

As shown in FIG. 9, a measuring instrument 70 mainly includes a blood sugar level measuring circuit 72 which measures a blood sugar level from the blood of a material to be measured, connector electrodes A and B allowing electrical connection to the blood sugar level measuring circuit 72 through sensor electrodes 62 and 63 of a biosensor chip 60, a sensor insertion determining circuit 71 which determines insertion of the biosensor chip 60, and connector electrodes C and D allowing electrical connection to the sensor insertion determining circuit 71 through a sensor electrode of the biosensor chip 60.

On the other hand, the biosensor chip 60 inserted into the measuring instrument 70 mainly includes the sensor electrode 62 which comes in contact with the connector electrode A, the sensor electrode 63 which comes in contact with the connector electrode B, the sensor electrode 64 which comes in contact with the connector electrodes C and D, and a blood sugar level sensor portion 61 formed to extend such that electrical connection with the sensor electrodes 62 and 63 can be made.

When the biosensor chip 60 is inserted into the measuring instrument 70, the connector electrode C and the connector electrode D are short-circuited by the sensor electrode 64. Accordingly, the sensor insertion determining circuit 71 determines insertion of the biosensor chip 60. After determining the sensor insertion, a user drops blood onto the blood sugar level sensor portion 61, and electric charges are generated by enzyme reaction of the dropped blood. Then, when a predetermined voltage is applied from the blood sugar level measuring circuit 72 after a predetermined period of time of neglect, an element current according to the enzyme reaction flows. Measurement of a blood sugar level is performed by displaying a value equivalent to the element current value generated by the oxidation on a display unit (not shown) of the measuring instrument 70.

In addition, Patent Document 2 discloses a bio-sensing meter in which two contact points are provided in each of detection electrode and excitation electrode in order to determine whether or not a sample piece has been inserted properly and which is set to detect that the sample piece has been inserted when either ones of the contact points are short-circuited.

In addition, Patent Document 3 discloses a measuring apparatus configured to determine mounting of a measuring sensor by using a thermistor in which a change of an electric resistance value to a temperature is large. A thermistor and a temperature detection circuit are provided in the measuring apparatus, the thermistor is connected to the temperature detection circuit when the measuring sensor is mounted in the measuring apparatus, and mounting of the measuring sensor is determined by outputting a temperature detection signal of a voltage value corresponding to a temperature measurement signal from the thermistor.

Patent Document 1: JP-A-11-108879
Patent Document 2: JP-T-08-504953
Patent Document 3: JP-A-2002-257782

DISCLOSURE OF THE INVENTION

Problems to be Solved by the Invention

However, in the measuring instrument 70 shown in FIG. 9, two electrodes of the connector electrodes C and D should be newly provided for the sensor insertion determining circuit in addition to providing the connector electrodes A and B at a side of the blood sugar level measuring circuit 72. In addition, according to the measuring apparatus disclosed in Patent Document 2, it is necessary to provide four contact points in order to determine whether or not the sample piece has been inserted correctly. Thus, four terminals are needed as terminals for the sensor in the measuring apparatus. If the number of mechanical contact points is increased, the reliability is lowered and the product life becomes short. Furthermore, in Patent Document 1, three terminals are required for an element reaction sensor member (biosensor chip). Accordingly, the size becomes large.

Therefore, it is an object of the present invention to make a biosensor chip small, to improve the reliability of a measuring instrument, and to make the product life long in the measuring instrument which determines whether or not a biosensor chip has been inserted and measures biological information on a biological material supplied to the biosensor chip. Furthermore, it is an object of the present invention to provide a biosensor chip configured to suppress a measurement error of biological information when measuring the biological information by inserting the biosensor chip, which has a sensor electrode formed of an electrode member with an electric resistance value higher than a conductive metal, into the measuring instrument.

Means for Solving the Problems

In order to achieve the above objects, there is provided a biosensor system including:

a biosensor chip; and a measuring instrument which measures biological information on a biological material supplied to the biosensor chip, wherein the biosensor chip includes: a reaction portion which is formed to be electrically connected to a plurality of sensor electrodes and to which the biological material is supplied, and the measuring instrument includes:

an insertion determining circuit which determines attachment and detachment of the biosensor chip;

a biological information measuring circuit which measures the biological information;

an insertion portion into which the biosensor chip can be inserted;

an insertion determining circuit side connector electrode which is electrically connected to the insertion determining circuit and is provided to come in contact with a first sensor electrode when the biosensor chip is inserted into the insertion portion;

a measuring circuit side connector electrode which is electrically connected to the biological information measuring circuit and is provided to come in contact with a second sensor electrode when the biosensor chip is inserted into the insertion portion; and a ground electrode provided to come in electrical contact with the first sensor electrode when the biosensor chip is inserted into the insertion portion.

Furthermore, it is preferable that the sensor electrodes are formed of a sensor electrode member having an electric resistance value higher than a conductive metal. In particular, it is preferable that the sensor electrode member is carbon.

Furthermore, according to the present invention, there is provided a measuring instrument including:

an insertion determining circuit which determines attachment and detachment of a biosensor chip;

a biological information measuring circuit which measures biological information;

an insertion portion into which the biosensor chip can be inserted;

an insertion determining circuit side connector electrode which is electrically connected to the insertion determining circuit and is provided to come in contact with a first sensor electrode when the biosensor chip is inserted into the insertion portion;

a measuring circuit side connector electrode which is electrically connected to the biological information measuring circuit and is provided to come in contact with a second sensor electrode when the biosensor chip is inserted into the insertion portion; and a ground electrode provided to come in electrical contact with the first sensor electrode when the biosensor chip is inserted into the insertion portion.

Furthermore, it is preferable that the measuring instrument, further including:

a voltage switching section capable of switching a voltage applied to the insertion determining circuit side connector electrode to a reference voltage or a ground potential, wherein the voltage switching section is set to perform switching from the reference voltage to the ground potential after determination on insertion of the biosensor chip by the sensor insertion determining circuit.

In addition, according to the present invention, there is provided a biosensor chip attachable to or detachable from a measuring instrument that includes a sensor insertion determining circuit which determines attachment and detachment of the biosensor chip, a biological information measuring circuit which measures biological information, an insertion portion into which the biosensor chip can be inserted, an insertion determining circuit side connector electrode which is electrically connected to the sensor insertion determining circuit and is provided in the insertion portion, a measuring circuit side connector electrode which is electrically connected to the biological information measuring circuit and is provided in the insertion portion, and a ground electrode provided in the insertion portion, the biosensor chip including:

a reaction portion to which a biological material is supplied;

a first sensor electrode provided to come in contact with the insertion determining circuit side connector electrode when inserted into the insertion portion;

a second sensor electrode provided such that one end thereof comes in contact with the measuring circuit side connector electrode and the other end is electrically connected to the reaction portion when inserted into the insertion portion; and a third sensor electrode provided such that one end thereof comes in contact with the ground electrode and the other end is electrically connected to the reaction portion when inserted into the insertion portion, wherein the first sensor electrode is electrically connected to the reaction portion through the third sensor electrode.

In addition, it is preferable that the first sensor electrode and the second sensor electrode are formed of a member having an electric resistance value higher than a conductive metal. In particular, it is preferable that the first sensor electrode and the second sensor electrode are formed of carbon.

EFFECTS OF THE INVENTION

According to the present invention, since the measuring instrument is configured such that the ground electrode is used in both the sensor insertion determining circuit and the blood sugar level measuring circuit and four connector electrodes provided in a known measuring instrument are reduced to three, the terminal number of electrodes is reduced compared with the known measuring instrument. As a result, since the number of mechanical contact points is reduced, the reliability is improved and a product life becomes long.

In addition, since the first sensor electrode of the biosensor chip can be shared by the sensor insertion determining circuit and the blood sugar level measuring circuit, three electrodes in the related art can be reduced to two. As a result, it is possible to make the biosensor chip small and to suppress a manufacturing cost.

In addition, according to the biosensor chip of the present invention, a measurement error of biological information can be suppressed in measuring the biological information by inserting the biosensor chip, which has a sensor electrode formed of a sensor electrode member with an electric resistance value higher than a conductive metal, into the measuring instrument.

DESCRIPTION OF REFERENCE NUMERALS AND SIGNS 1, 41: measuring instrument
5, 45: insertion portion
11, 51: measuring circuit side connector electrode
13, 53: insertion determining circuit side connector electrode
12, 52: ground electrode
14, 54: sensor insertion determining circuit
15, 55: blood sugar level measuring circuit (biological information measuring circuit)
Ref: reference voltage
GND: ground voltage
20, 30: biosensor chip
21, 31: first sensor electrode
22, 32: second sensor electrode
23, 33: blood sugar level sensor portion (biological material sensor portion)
R1, R2: pull-up resistor
SW: switch (voltage switching mechanism)

BEST MODE FOR CARRYING OUT THE INVENTION

Hereinafter, embodiments of a biosensor chip, a biosensor system, and its measuring instrument according to the present invention will be described in detail with reference to the accompanying drawings. Moreover, in the present embodiment, blood is mentioned as an example of a biological material supplied to the biosensor chip and the measuring instrument will be described by using a biosensor system, which is a measuring instrument that measures a blood sugar level in the blood, as an example.

Figure 1:
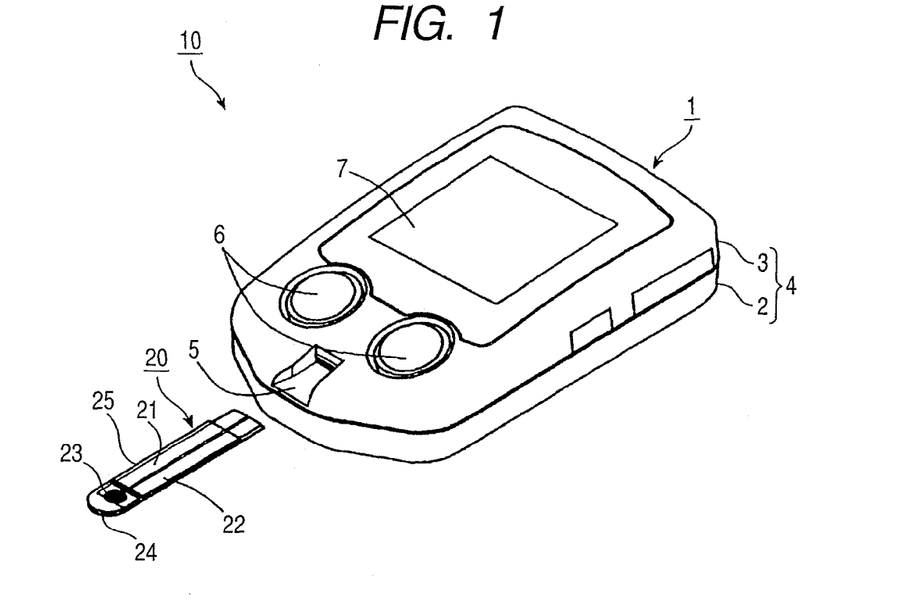
FIG. 1 is a perspective view illustrating the appearance of a biosensor system according to a first embodiment of the present invention.

FIG. 1 is a perspective view illustrating the appearance of a biosensor system according to a first embodiment of the present invention.

Figure 2:
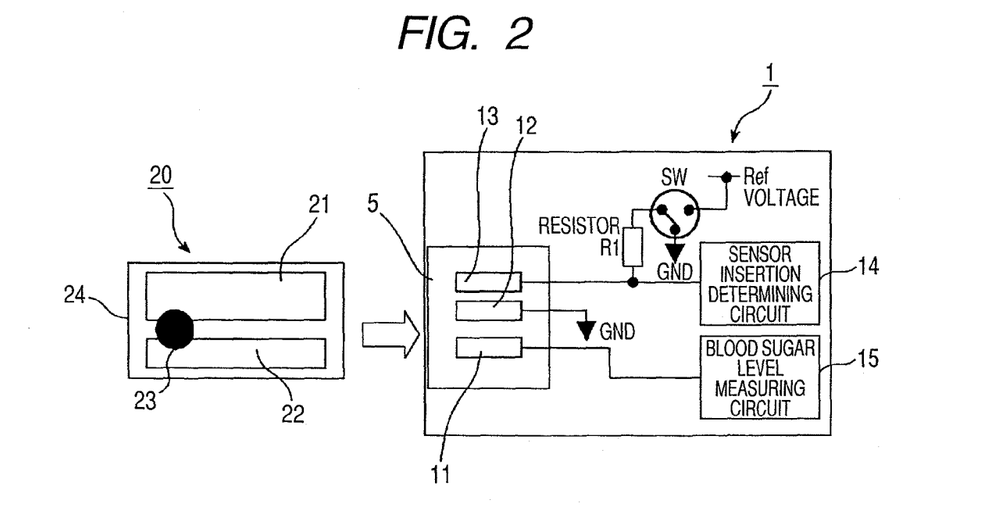
FIG. 2 is a view illustrating the configuration of main parts of the biosensor system according to the first embodiment of the present invention.

FIG. 2 is a block diagram illustrating the configuration of main parts of the biosensor system of FIG. 1.

Figure 3:
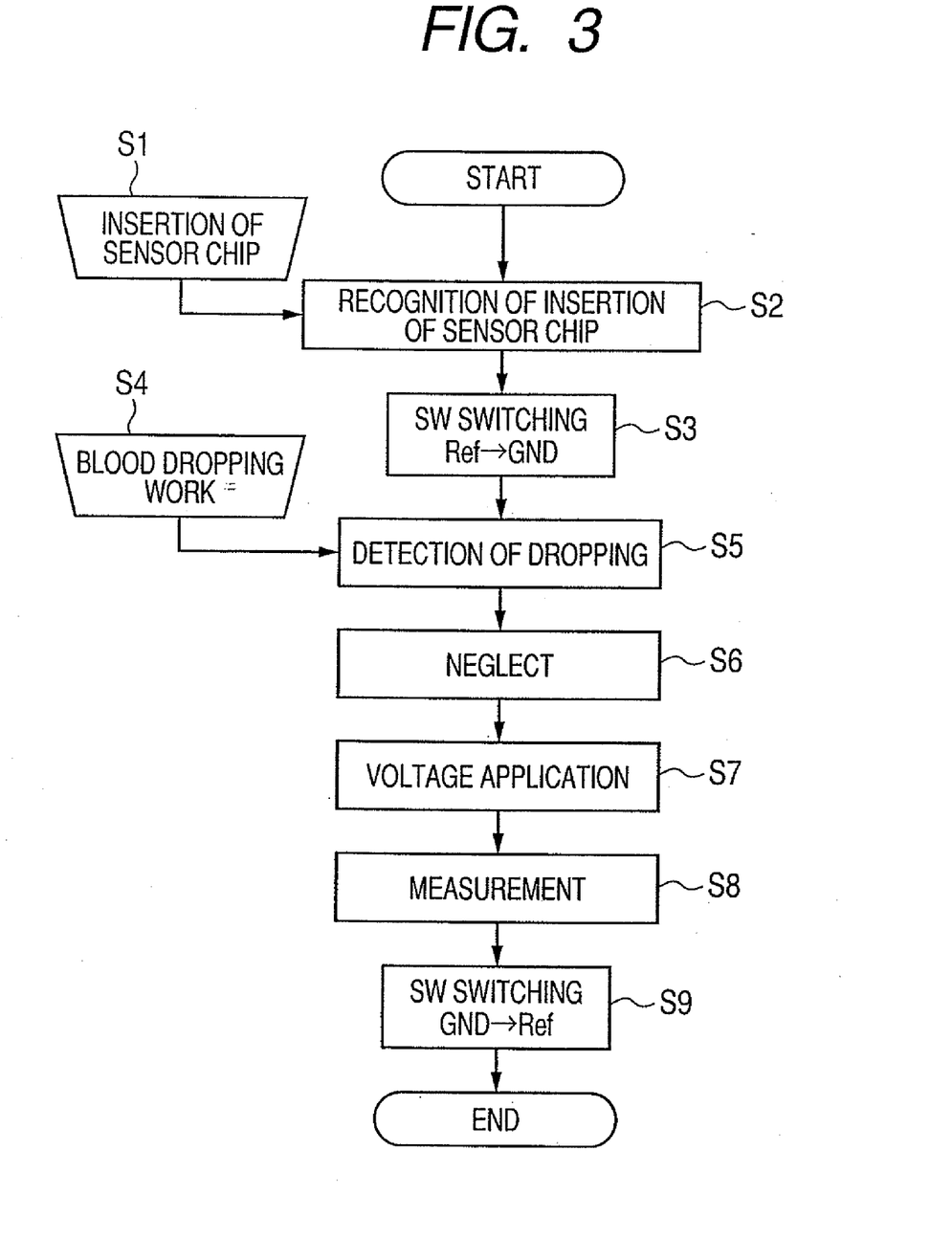
FIG. 3 is a flow chart explaining a blood sugar level measuring process performed by a measuring instrument in the biosensor system according to the first embodiment of the present invention.

FIG. 3 is a flow chart explaining a blood sugar level measuring process in the biosensor system according to the first embodiment of the present invention.

Figure 4:
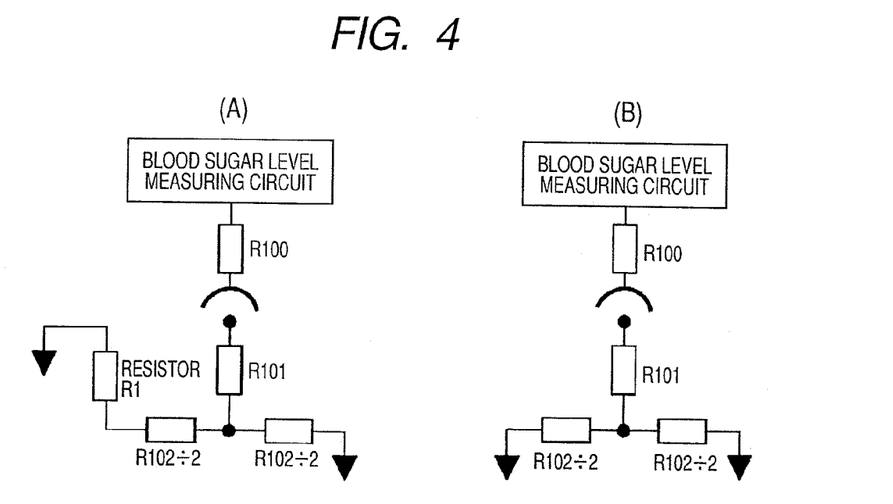
FIG. 4 is an equivalent circuit diagram of the measuring instrument in the biosensor system according to the first embodiment of the present invention.

FIG. 4 is an equivalent circuit diagram of the main parts of the biosensor system according to the first embodiment of the present invention.

Figure 5:
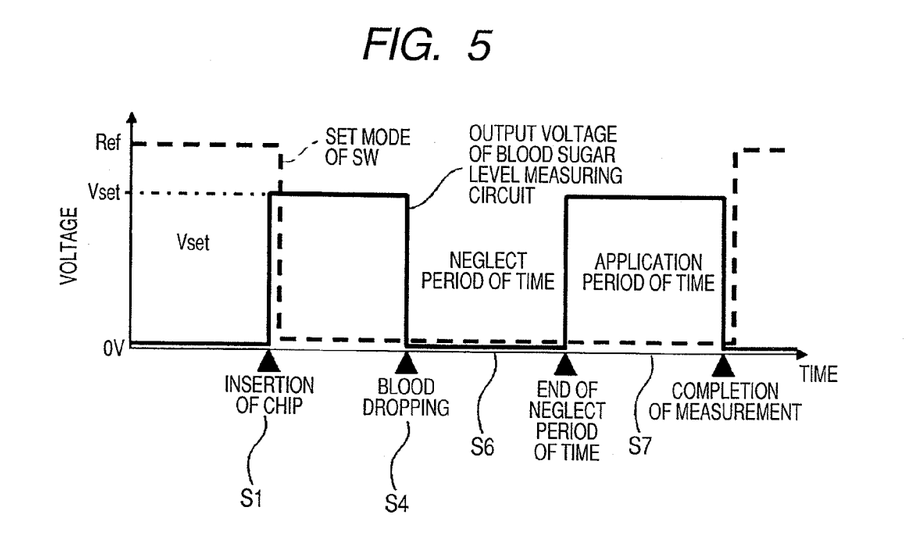
FIG. 5 is a graph illustrating the time course of a voltage applied to the measuring instrument of the biosensor system according to the first embodiment of the present invention.

FIG. 5 is a graph illustrating the time course of a voltage applied to a measuring instrument of the biosensor system according to the first embodiment of the present invention.

First, the appearance of the biosensor system 10 according to the first embodiment of the present invention will be described.

The biosensor system 10 shown in FIG. 1 includes a detachable biosensor chip 20 and a measuring instrument 1 which determines whether or not the biosensor chip 20 is inserted and measures the blood sugar level (biological information) in the blood (biological material) supplied to the biosensor chip 20.

As shown in FIG. 1, in the measuring instrument 1, an insertion portion 5 into which the biosensor chip 20 is inserted is opened in the front middle of a housing 4 configured to include a lower case 2 and an upper housing 3, and circular operation buttons 6 and 6 are provided at rear left and right sides of the insertion portion 5.

In addition, a rectangular display unit 7 which displays the measured blood sugar level is provided at a side behind the operation buttons 6 and 6. Electrodes (an insertion determining circuit side connector electrode 13, a measuring circuit side connector electrode 11, a ground electrode 12) that can come in electrical contact with electrodes provided in the biosensor chip 20 when the biosensor chip 20 is inserted into the insertion portion 5 are provided, which will be described in detail later (refer to FIG. 2).

As shown in FIG. 1, in the biosensor chip 20, a first sensor electrode 21 and a second sensor electrode 22 parts of which come in electrical contact with the electrodes of the measuring instrument 1 when inserted into the insertion portion 5 of the measuring instrument 1 are provided on a stick-shaped insulating substrate 24, which may be inserted into the insertion portion 5 of the measuring instrument 1, so as to be approximately parallel to each other along the longitudinal direction.

Furthermore, near an end opposite the side inserted into the measuring instrument, a reaction portion 23 to which blood (biological material) is supplied is provided to extend such that electrical connection with the first sensor electrode 21 and the second sensor electrode 22 is made.

In addition, a portion of each of the electrodes 21 and 22 excluding a portion, which comes in electrical contact with each electrode of the measuring instrument 1, and a portion, which is electrically connected to the blood sugar level sensor portion 23, may be covered with a film 25 formed of an insulating material.

Next, an example of a method of forming the biosensor chip 20 will be described.

For the insulating substrate 24 which forms the main body of the biosensor chip 20, ceramics, glass, paper, biodegradable materials (for example, microbially-produced polyester), and plastic materials such as polyethylene terephthalate are used as materials.

A pair of sensor electrodes of the first sensor electrode 21 and the second sensor electrode 22 described above is patterned on the insulating substrate 24 in order to take out an element current generated by enzyme reaction of oxidoreductase, for example. For the sensor electrode members, not only conductive metals, such as silver, gold, palladium, platinum, nickel, copper, and iridium, but also non-metallic materials having electric resistance values higher than the conductive metals, such as carbon and conductive plastics (including not only polyacethylene, poly-ρ-phenylene, polypyrrole, and polythiophene, each of which has conductivity in itself, but also plastics mixed with conductive metallic particles) may be used. A pattern of the sensor electrode members is formed by screen printing, bonding, vapor deposition, sputtering, and the like. In addition, since the disposable biosensor chip 20 is usually used, carbon which is cheap and is easy to be formed as an electrode is more preferable.

The blood sugar level sensor portion 23 may be formed of a mixture of oxidoreductase and an electron carrier (mediator), for example, a mixture of glucose oxidase and potassium ferricyanide.

In the case of a disposable glucose biosensor using the glucose oxidase which is a typical oxidoreductase, a sample of an object to be measured is mostly taken to perform measurement.

A method of indirectly obtaining the glucose concentration with an element current value by oxidation-reduction reaction is already known. A ferricyanide ion is reduced to a ferrocyanide ion and gluconolactone is generated by glucose oxidase reaction, and the ferrocyanide ion is oxidized and the element current value is detected and measured.

Next, the configuration of the main parts of the biosensor system 10 according to the first embodiment of the present invention will be described in detail.

As shown in FIG. 2, the measuring instrument 1 includes a sensor insertion determining circuit 14 as a determining means for recognizing whether or not the biosensor chip 20 is inserted into the main body of the measuring instrument and is in a measurable state. In addition, there is included a blood sugar level measuring circuit 15 which measures a measurement value (that is, a blood sugar level) of an element current value of the blood, which is a material to be measured, after detecting that the biosensor chip 20 has been inserted.

In addition, there is included the insertion determining circuit side connector electrode 13 which is electrically connected to the sensor insertion determining circuit 14 and which is provided to come in contact with the first sensor electrode 21 provided in the biosensor chip 20 when the biosensor chip 20 is inserted.

In addition, there is included the measuring circuit side connector electrode 11 which is electrically connected to the blood sugar level measuring circuit 15 and which is provided to come in contact with the second sensor electrode 22 provided in the biosensor chip 20 when the biosensor chip 20 is inserted.

In addition, there is included the ground electrode 12 which is connected to a ground potential GND and which is provided to come in contact with the first sensor electrode 21 provided in the biosensor chip 20 when the biosensor chip 20 is inserted.

As described above, the measuring instrument 1 has a configuration in which the ground electrode 12 is used in both the sensor insertion determining circuit 14 and the blood sugar level measuring circuit 15. Thus, since four connector electrodes provided in a known measuring instrument are reduced to three, the terminal number of electrodes in the measuring instrument 1 of the biosensor system according to the present embodiment is reduced compared with the known measuring instrument. As a result, since the number of mechanical contact points is reduced, the reliability is improved and a product life becomes long.

In addition, since the first sensor electrode 21 of the biosensor chip 20 can also be shared by the sensor insertion determining circuit 14 and the blood sugar level measuring circuit 15 as shown in FIG. 2, three electrodes in the related art can be reduced to two. Accordingly, it is possible to make the biosensor chip 20 small and to suppress a manufacturing cost.

In the present embodiment, when the biosensor chip 20 is inserted into the measuring instrument 1, a closed circuit state is formed from an open circuit state before insertion by short circuiting between the first sensor electrode 21 and the ground electrode 12 connected to the ground potential GND and the insertion determining circuit side connector electrode 13 after insertion, a voltage is applied between the insertion determining circuit side connector electrode 13 and the ground electrode 12 by connection to a reference voltage Ref, and the sensor insertion determining circuit 14 determines whether or not the biosensor chip 20 has been inserted.

As a portion which makes an overall control of the measuring instrument 1, a control unit (not shown), such as a CPU (central processing unit), by a microcomputer is provided in the measuring instrument 1. This control unit is configured to include a current voltage conversion circuit which converts an element current detected in the blood sugar level measuring circuit 15 into a voltage value, an amplifying circuit which amplifies the converted voltage signal, and an operation portion which performs operation processing on the basis of the input data signal and is configured such that a value processed in the operation portion is displayed as measurement data on the display unit 7. The CPU makes an overall control on the basis of a signal that is input and output through an I/O port from each circuit of each portion.

In addition, a pull-up resistor R1 is connected between the insertion determining circuit side connector electrode 13 and the sensor insertion determining circuit and a voltage switching section (hereinafter, referred to as a switch) SW for switching a voltage, which is applied to the insertion determining circuit side connector electrode 13 and the ground electrode 12, to the reference voltage Ref or the ground potential GND is provided between the pull-up resistor R1 and the reference voltage Ref.

By connecting the pull-up resistor R1, an input level to the sensor insertion determining circuit 14 can be set to 'High' in a state where the switch SW is connected to the reference voltage Ref.

Then, when the biosensor chip 20 is inserted from the insertion portion 5 in the state where switch SW is connected to the reference voltage Ref, the insertion determining circuit side connector electrode 13 and the ground electrode 12 are short-circuited by the first sensor electrode 21. As a result, 'Low' is input to the sensor insertion determining circuit 14. Thus, the measuring instrument 1 can determine that the biosensor chip 20 has been inserted from the insertion portion 5 when the input level to the sensor insertion determining circuit 14 changes from 'High' to 'Low'.

Meanwhile, since the biosensor chip 20 is usually of a disposable type, the cost is increased if electrodes (the first sensor electrode 21 and the second sensor electrode 22) are formed of metal. Accordingly, it is preferable to form the electrodes with a cost of a member itself or a member (for example, carbon) which is cheap in manufacturing electrodes if possible.

Hereinafter, an explanation will be made by using the biosensor chip 20 formed of carbon, which is cheap and is simple in terms of manufacturing, as an example.

Since carbon is a member having a higher electric resistance value than a conductive metal, the first sensor electrode 21 holds an electric potential by inter-electrode resistance between the insertion determining circuit side connector electrode 13 and the ground electrode 12 when the insertion determining circuit side connector electrode 13 and the ground electrode 12 are short-circuited by the first sensor electrode 21.

When the first sensor electrode 21 has an electric potential (V0) during measurement of a blood sugar level, an electric potential (−V0) of the first sensor electrode 21 is also applied since only a predetermined voltage (Vset) applied between the measuring circuit side connector electrode 11 and the ground electrode 12 from the blood sugar level measuring circuit 15 should be applied during the blood sugar level measurement.

Accordingly, in the case of adopting the biosensor chip 20 having electrodes formed of carbon like the present embodiment, the insertion determining circuit side connector electrode 13 and the ground electrode 12 are set to be equipotential by switching the switch SW from the reference voltage Ref to the ground potential GND after the biosensor chip 20 is inserted into the insertion portion 5 of the measuring instrument 1 and insertion of the biosensor chip 20 is determined by the sensor insertion determining circuit 14. That is, a state where the reference voltage Ref is not applied is set while the blood sugar level measuring circuit 15 is measuring a blood sugar level.

The measuring instrument 1 shown in FIG. 2 is in a state where the switch SW switches from the reference voltage Ref to the ground potential GND, and FIG. 4A shows the equivalent circuit.

Taking electric resistance values of the first sensor electrode 21 and second sensor electrode 22 into consideration, resistance that the first sensor electrode 21 has is set to R101 (about 2.7 [KΩ]) and resistance that the second sensor electrode 22 has is set to R100 (about 2.7 [KΩ]).

Assuming that carbon electrode resistance between the insertion determining circuit side connector electrode 13 and the ground electrode 12 is to R102 (about 100 [Ω]) and R101>>R102, the insertion determining circuit side connector electrode 13 and the ground electrode 12 are short-circuited through the first sensor electrode 21 in a state where the reference voltage Ref is always applied between the insertion determining circuit side connector electrode 13 and the ground electrode 12. Accordingly, a voltage V0 (=Ref× R102÷2(R1+R102)) obtained when the reference voltage Ref is voltage-divided into R1 and R102 is applied to the first sensor electrode 21.

Although 0 [V] should be applied during a neglect period of the blood sugar level measurement, the ground electrode 12 is set to the ground potential GND. Accordingly, ground potential GND (0V)-V0 is applied between the ground electrode 12 and the measuring circuit side connector electrode 11.

Moreover, in an application period, (Vset)-V0 is applied to the ground electrode 12 and the measuring circuit side connector electrode 11 since the predetermined voltage (Vset) should be applied from the blood sugar level measuring circuit 15.

Thus, since a case where a measured blood sugar level is output as a low value may be considered, the insertion determining circuit side connector electrode 13 and the ground electrode 12 are set to be equipotential and V0 becomes 0 [V] by causing the switch SW to perform switching from the reference voltage Ref to the ground potential GND in application period and neglect period.

In addition, the same effects may be obtained by realizing an equivalent circuit shown in FIG. 4B. That is, the switch SW may be provided between the insertion determining circuit side connector electrode 13 and the pull-up resistor R1 so that the insertion determining circuit side connector electrode 13 can be selected to the ground potential GND or the sensor insertion determining circuit 14 can output 0 [V].

Moreover, if the first sensor electrode 21 and the sensor electrode 22 are formed of silver paste with a low electric resistance value, for example, in addition to being formed of a member having an electric resistance value higher than metal, such as carbon, a measurement error caused by the potential difference between the insertion determining circuit side connector electrode 13 and the ground electrode 12 can be reduced. As a result, since the switch SW does not need to be provided, an operation of switching from the reference voltage Ref to the ground potential GND can be omitted. However, since the silver paste is relatively more expensive than carbon, the cost of a biosensor chip is raised.

In addition, by applying the reference voltage Ref all the time, it can be easily determined that the biosensor chip 20 has been attached or detached since the input level of the sensor insertion determining circuit 14 changes from 'Low' to 'High' even if the biosensor chip 20 is attached to or detached from the insertion portion 5 during the blood sugar level measurement.

Next, blood sugar level measuring process of the measuring instrument 1 will be described using FIGS. 2, 3, and 5.

First, the biosensor chip 20 is inserted from the insertion portion 5 of the measuring instrument 1 (step S1).

In a step of inserting the biosensor chip 20, sampled blood to be measured is not yet dropped onto the blood sugar level sensor portion 23 of the biosensor chip 20.

Accordingly, an open circuit still exists between the first sensor electrode 21 and the second sensor electrode 22 of the biosensor chip 20. By insertion of the biosensor chip 20, the first sensor electrode 21 is connected to the insertion determining circuit side connector electrode 13 and the ground electrode 12 of the measuring instrument 1 and the second sensor electrode 22 is connected to the measuring circuit side connector electrode 11. Then, a change to a short-circuited state occurs to form a closed circuit, and the reference voltage Ref is connected to the sensor insertion determining circuit 14 to thereby start the measuring instrument 1.

The control unit recognizes that the biosensor chip 20 has been inserted when the input level of the sensor insertion determining circuit 14 changes from 'High' to 'Low' (step S2).

When insertion of the biosensor chip 20 is recognized, the voltage (Vset) is applied between the ground electrode 12 and the measuring circuit side connector electrode 11 by a control signal output from the control unit. At the same time, the switch SW switches from the reference voltage Ref to the ground potential GND (step S3).

Then, when the blood to be measured drops onto the blood sugar level sensor portion 23 of the biosensor chip 20 (step S4), the ground electrode 12 and the measuring circuit side connector electrode 11 are short-circuited to form a closed circuit.

The control unit determines that the blood has dropped on the basis of the closed signal (step S5), and supply of the voltage (Vset) which has been applied between the ground electrode 12 and the measuring circuit side connector electrode 11 is stopped and neglected (step S6).

Supply of the applied voltage (Vset) is stopped in the neglect period in order to accumulate electric charges generated by chemical change of the blood to be measured. In synchronization with this, the control unit starts counting a remaining time from a numeric value of a time set beforehand to the end of measurement, for example, 30 seconds.

The remaining time that is counted is displayed on the display unit 7 so that a user can recognize it. When the remaining time reaches the setup time, the voltage (Vset) of a value set beforehand for reaction is applied again between the ground electrode 12 and the measuring circuit side connector electrode 11 this time (step S7).

In the blood dropped onto the blood sugar level sensor portion 23, reduction product generated by enzyme reaction is oxidized by the repeated voltage application and a value of an element current generated by the oxidation is detected and acquired (step S8).

After applying the voltage (Vset) for a predetermined period of time, the element current value that has been detected and acquired is converted into a voltage value in the blood sugar level measuring circuit 15 and the converted voltage value is amplified in the amplifying circuit.

Referring to a data table corresponding to the amplified voltage, data of a calculation result in the operation portion is displayed on the display unit 7. Then, the switch SW switches from the ground potential GND to the reference voltage Ref again (step S9).

By switching the switch SW from the ground potential GND to the reference voltage Ref after displaying the data of a measurement result for a predetermined period of time, the measuring instrument 1 can be automatically turned off by recognizing removal of the biosensor chip 20, since the input level of the sensor insertion determining circuit 14 changes from 'Low' to 'High' when the biosensor chip 20 is detached from the measuring instrument 1.

In addition, the measuring instrument 1 may also be set to be automatically turned off when the biosensor chip 20 has not been removed even if the biosensor chip 20 is not removed but is in a neglect state.

In the present embodiment, as shown in FIG. 5, the switch SW is configured to switch from the reference voltage Ref to the ground potential GND after insertion of the biosensor chip 20 is recognized and switch from the ground potential GND to the reference voltage Ref to after the blood sugar level is measured (refer to a voltage change shown by a dotted line in FIG. 5).

Accordingly, until the blood sugar level is measured after the biosensor chip 20 is inserted, a potential difference based on inter-electrode resistance between the insertion determining circuit side connector electrode 13 and the ground electrode 12 caused by the first sensor electrode 21 formed of carbon does not occur.

Thus, since the applied voltage is set to 0 [V] during the neglect period (step S6) and the predetermined voltage (Vset) is reliably applied in the application period (step S7), a more accurate blood sugar level (measurement value) can be obtained.

By providing a voltage switching section (switch SW) that is set to switch a voltage applied to the insertion determining circuit side connector electrode from a reference voltage to a ground voltage after determination on insertion of the biosensor chip is performed by the sensor insertion determining circuit, a more accurate measurement value can be obtained because the potential difference (corresponding to the first sensor electrode that is a member having an electric resistance value higher than a conductive metal) occurring when the insertion determining circuit side connector electrode and the ground electrode are connected to each other through the first sensor electrode does not arise.

Next, a second embodiment of the biosensor chip according to the present invention will be described in detail with reference to the accompanying drawings. Moreover, in the present embodiment, blood is mentioned as an example of a biological material supplied to a biosensor chip, a measuring instrument that uses the biosensor chip is a measuring instrument that measures a blood sugar level of the blood, and an example of a biosensor system configured to include the biosensor chip and the measuring instrument is mentioned to thus make an explanation.

Figure 6:
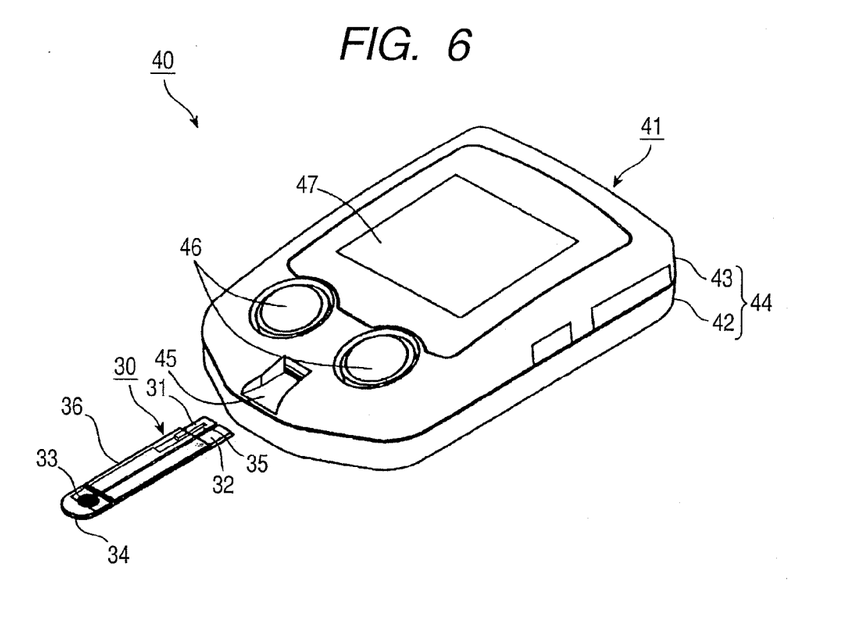
FIG. 6 is a perspective view illustrating the appearance of a biosensor system which uses a biosensor chip according to a second embodiment of the present invention.

FIG. 6 is a perspective view illustrating the appearance of a biosensor system which uses a biosensor chip according to the second embodiment of the present invention.

Figure 7:
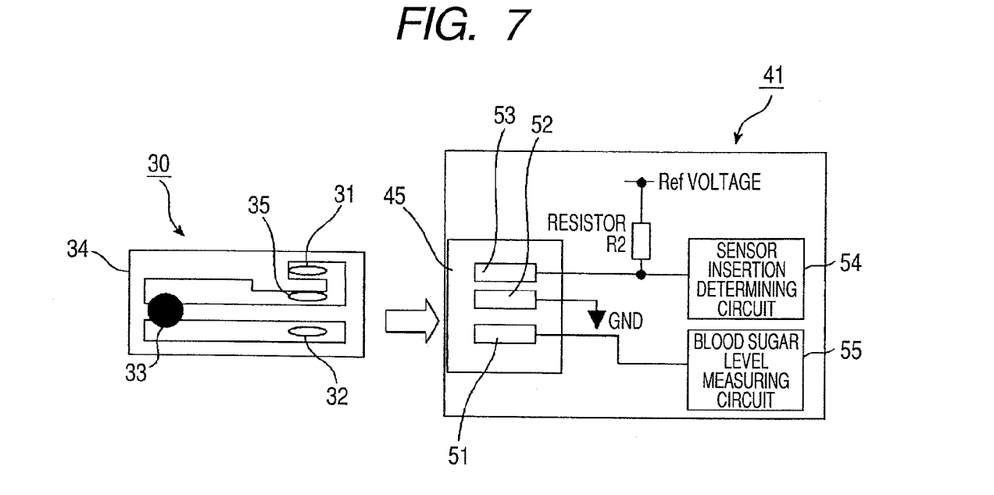
FIG. 7 is a view illustrating the configuration of main parts of the biosensor system of FIG. 6.

FIG. 7 is a block diagram illustrating the configuration of main parts of the biosensor system of FIG. 6.

First, the appearance of a biosensor system 40 will be described.

The biosensor system 40 shown in FIG. 6 includes a detachable biosensor chip 30 and a measuring instrument 41 which determines whether or not a biosensor chip 20 is inserted and measures the blood sugar level (biological information) in the blood (biological material) supplied to the biosensor chip 30.

As shown in FIG. 6, in the measuring instrument 41, an insertion portion 45 into which the biosensor chip 30 is inserted is opened in the front middle of a housing 44 configured to include a lower case 42 and an upper housing 43, and circular operation buttons 46 and 46 are provided at rear left and right sides of the insertion portion 45. In addition, a rectangular display unit 47 which displays the measured blood sugar level is provided at a side behind the operation buttons 46 and 46. Electrodes (an insertion determining circuit side connector electrode 53, a measuring circuit side connector electrode 51, a ground electrode 52) that can come in electrical contact with electrodes provided in the biosensor chip 30 when the biosensor chip 30 is inserted into the insertion portion 45 are provided, which will be described in detail later (refer to FIG. 7).

In the biosensor chip 30, a first sensor electrode 31, a second sensor electrode 32, and a third sensor electrode 35 are provided on a stick-shaped insulating substrate 34, which may be inserted into the insertion portion 45 of the measuring instrument 41, so as to be approximately parallel to one another along the longitudinal direction.

The first sensor electrode 31 is provided to come in contact with the insertion determining circuit side connector electrode 13 of the measuring instrument 41 when inserted into the insertion portion 45 of the measuring instrument 41.

The second sensor electrode 32 is provided such that one end thereof comes in contact with the measuring circuit side connector electrode 51 and the other end is electrically connected to the following blood sugar level sensor portion 33 when inserted into the insertion portion 45 of the measuring instrument 41.

The third sensor electrode 35 is provided such that one end thereof inserted into the measuring instrument comes in contact with a ground electrode and the other end is electrically connected to the following blood sugar level sensor portion 33 when inserted into the insertion portion 45 of the measuring instrument 41. That is, the first sensor electrode 31 is electrically connected to the following blood sugar level sensor portion 33 through the third sensor electrode 35.

Furthermore, near an end opposite the side inserted into the measuring instrument 41, a blood sugar level sensor portion (reaction portion) 33, which is formed in the approximately circular shape to extend such that electrical connection with the third sensor electrode 35 and the second sensor electrode 32 is made and to which blood (biological material) is supplied, is provided.

In addition, a portion of each of the electrodes 31, 32, and 35 excluding a portion, which comes in electrical contact with each electrode of the measuring instrument 41, and a portion, which is electrically connected to the blood sugar level sensor portion 33, may be covered with a film 36 formed of an insulating material.

Next, an example of a method of forming the biosensor chip 30 will be described.

For the insulating substrate 34 which forms the main body of the rectangular biosensor chip 30, ceramics, glass, paper, biodegradable materials (for example, microbially-produced polyester), and plastic materials such as polyethylene terephthalate are used as materials. Sensor electrodes including the first sensor electrode 31, the second sensor electrode 32, and the third sensor electrode 35 for taking out an element current generated by enzyme reaction of oxidoreductase, for example, are formed on the insulating substrate 34. For the sensor electrode members, not only conductive metals, such as silver, gold, palladium, platinum, nickel, copper, and iridium, but also non-metallic materials having electric resistance values higher than the conductive metals, such as carbon and conductive plastics (including not only polyacethylene, poly-p-phenylene, polypyrrole, and polythiophene, each of which has conductivity in itself, but also plastics mixed with conductive metallic particles) may be used. A pattern of the sensor electrode members is formed by screen printing, bonding, vapor deposition, sputtering, and the like. In addition, since the disposable biosensor chip 30 is usually used, carbon which is cheap and is easily formed as an electrode is more preferable.

The blood sugar level sensor portion 33 may be formed of a mixture of oxidoreductase and an electron carrier (mediator), for example, a mixture of glucose oxidase and potassium ferricyanide. In the case of a disposable glucose biosensor using the glucose oxidase which is a typical oxidoreductase, an undiluted sample of an object to be measured is mostly taken to perform measurement. A method of indirectly obtaining the glucose aqueous solution concentration with an element current value by oxidation is already known. A ferricyanide ion is reduced to a ferrocyanide ion and gluconolactone is generated by glucose oxidase reaction, and the ferrocyanide ion is oxidized and the element current value is detected and measured.

Next, the configuration of main parts of the biosensor system shown in FIG. 6 will be described with reference to FIG. 7.

As shown in FIG. 7, the measuring instrument 41 includes a sensor insertion determining circuit 54 as a determining means for recognizing whether or not the biosensor chip 20 is inserted into the main body of the measuring instrument and is in a measurable state. In addition, there is included a blood sugar level measuring circuit 15 which measures a measurement value (that is, a blood sugar level) of an element current value of the blood, which is a material to be measured, after detecting that the biosensor chip 30 has been inserted.

In addition, there is included the insertion determining circuit side connector electrode 53 which is electrically connected to the sensor insertion determining circuit 54 and which is provided to come in contact with the first sensor electrode 31 provided in the biosensor chip 30 when the biosensor chip 30 is inserted.

In addition, there is included the measuring circuit side connector electrode 51 which is electrically connected to the blood sugar level measuring circuit 55 and which is provided to come in contact with the second sensor electrode 32 provided in the biosensor chip 30 when the biosensor chip 30 is inserted.

In addition, there is included the ground electrode 52 which is connected to the ground potential GND and which is provided to come in contact with the third sensor electrode 35 provided in the biosensor chip 30 when the biosensor chip 30 is inserted.

As described above, the measuring instrument 41 has a configuration in which the ground electrode 52 is used in both the sensor insertion determining circuit 54 and the blood sugar level measuring circuit 55.

Thus, since four connector electrodes provided in a known measuring instrument are reduced to three, a space for one electrode is not needed compared with the known measuring instrument. As a result, a housing can be made small. In addition, the manufacturing cost of the measuring instrument 41 can be suppressed by miniaturization of the housing, reduction of a member corresponding to one electrode, reduction of a ground circuit, and the like.

In the present embodiment, when the biosensor chip 30 is inserted into the measuring instrument 41, the first sensor electrode 31 is connected to the insertion determining circuit side connector electrode 53 and the third sensor electrode 35 is connected to the ground electrode 52. Accordingly, the insertion determining circuit side connector electrode 53 and the ground electrode 52 are short-circuited, forming a closed circuit state from an open circuit state before insertion. In addition, the sensor insertion determining circuit 54 determines insertion of the biosensor chip 30 when a voltage is applied between the insertion determining circuit side connector electrode 53 and the ground electrode 52 by the reference voltage Ref.

As a portion which makes an overall control of the measuring instrument 41, a control unit (not shown), such as a CPU (central processing unit), by a microcomputer is provided in the measuring instrument 41. This control unit is configured to include a current voltage conversion circuit which converts an element current detected in the blood sugar level measuring circuit 55 into a voltage value, an amplifying circuit which amplifies the converted voltage signal, and an operation portion which performs operation processing on the basis of the input data signal and is configured such that a value processed in the operation portion is displayed as measurement data on the display unit 47. The CPU makes an overall control on the basis of a signal that is input and output through an I/O port from each circuit of each portion.

In addition, a pull-up resistor R2 is connected between the insertion determining circuit side connector electrode 53 and the sensor insertion determining circuit 54. By connecting the pull-up resistor R2, an input level to the sensor insertion determining circuit 54 can be set to 'High'. When the biosensor chip 30 is inserted from the insertion portion 45, the insertion determining circuit side connector electrode 53 and the ground electrode 52 are short-circuited. Accordingly, 'Low' is input to the sensor insertion determining circuit 54. Thus, the measuring instrument 41 can determine that the biosensor chip 30 has been inserted from the insertion portion 45 when the input level to the sensor insertion determining circuit 54 changes from 'High' to 'Low'.

Figure 8:
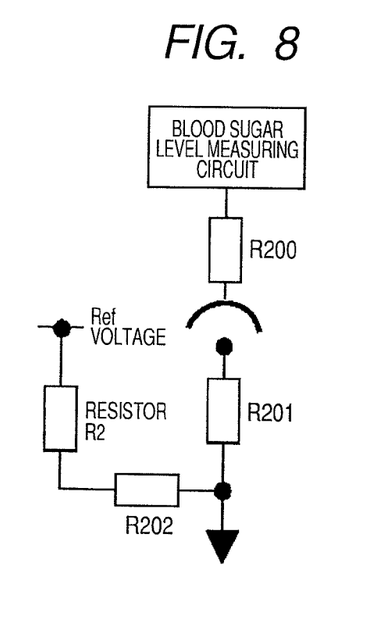
FIG. 8 is an equivalent circuit diagram explaining operations and effects when a biosensor chip according to the second embodiment of the present invention is used.

Next, operations and effects when using the biosensor chip according to the present embodiment will be described with reference to FIG. 8. FIG. 8 is an equivalent circuit diagram explaining operations and effects when the biosensor chip according to the present embodiment is used.

As shown in FIG. 8, for example, the resistance that the third sensor electrode 35 has is set to R201 (about 2.7 [K$\Omega$]) and the resistance that the second sensor electrode 32 has is set to R200 (about 2.7 [K$\Omega$]). In addition, assuming that the carbon electrode resistance between the insertion determining circuit side connector electrode 53 and the ground electrode 52 is R202 (about 100[$\Omega$]) and R201>>R202, the first sensor electrode 31 is connected to the blood sugar level sensor portion 33 through only the third sensor electrode 35. Accordingly, the reference voltage Ref is not divided by R2 and R202 during blood sugar level measurement.

That is, since the first sensor electrode 31 and the blood sugar level sensor portion 33 are not directly connected to each other, a divided voltage is not applied between the measuring circuit side connector electrode 51 and the ground electrode 52 unlike the example shown in FIG. 4.

Thus, also in a state where the reference voltage Ref is applied during blood sugar level measurement, only a voltage from the blood sugar level measuring circuit 55 is applied between the measuring circuit side connector electrode 51 and the ground electrode 52 during the blood sugar level measurement. Accordingly, it is possible to prevent a blood sugar level lower than the original blood sugar level from being output due to voltage division (V0), unlike the example shown in FIG. 4. As a result, since a relatively low blood sugar level can also be measured accurately, the measuring range of the measuring instrument 41 can be extended. As a result, a measurement error occurring when the biosensor chip 30 is inserted into the measuring instrument 41 to measure the blood sugar level can be suppressed.

While the present invention has been described with reference to the specific embodiments, it is apparent to those skilled in the art that various changes and modifications may be made without departing from the spirit and scope of the present invention. This application claims priority from Japanese Patent Applications (Patent Application Nos. 2006-50607 and 2006-50608) filed on Feb. 27, 2006, the entire content of which is incorporated herein by reference.

[FIG. 2]
A1: Ref VOLTAGE
R1: RESISTOR
14: SENSOR INSERTION DETERMINING CIRCUIT
15: BLOOD SUGAR LEVEL MEASURING CIRCUIT
[FIG. 3]
A1: START
S1: INSERTION OF SENSOR CHIP
S2: RECOGNITION OF INSERTION OF SENSOR CHIP
S3: SW SWITCHING
S4: BLOOD DROPPING WORK
S5: DETECTION OF DROPPING
S6: NEGLECT
S7: VOLTAGE APPLICATION
S8: MEASUREMENT
S9: SW SWITCHING
A2: END
[FIG. 4]
(A)
A1: BLOOD SUGAR LEVEL MEASURING CIRCUIT
R1: RESISTOR
(B)
A1: BLOOD SUGAR LEVEL MEASURING CIRCUIT
[FIG. 5]
A1: VOLTAGE
A2: SET MODE OF SW
A3: OUTPUT VOLTAGE OF BLOOD SUGAR LEVEL MEASURING CIRCUIT
A4: NEGLECT PERIOD OF TIME
A5: APPLICATION PERIOD OF TIME
A6: INSERTION OF CHIP
A7: BLOOD DROPPING
A8: END OF NEGLECT PERIOD OF TIME
A9: COMPLETION OF MEASUREMENT
A10: TIME
[FIG. 7]
A1: Ref VOLTAGE
R2: RESISTOR
54: SENSOR INSERTION DETERMINING CIRCUIT
55: BLOOD SUGAR LEVEL MEASURING CIRCUIT
[FIG. 8]
A1: BLOOD SUGAR LEVEL MEASURING CIRCUIT
A2: Ref VOLTAGE
R2: RESISTOR
[FIG. 9]
D: CONNECTOR ELECTRODE
C: CONNECTOR ELECTRODE
R1: RESISTOR
71: SENSOR INSERTION DETERMINING CIRCUIT
72: BLOOD SUGAR LEVEL MEASURING CIRCUIT
B: CONNECTOR ELECTRODE
A: CONNECTOR ELECTRODE
A1: CONNECTOR OF MEASURING INSTRUMENT

The invention claimed is:

1. A biosensor system comprising:
a biosensor chip; and
a measuring instrument which measures biological information on a biological material supplied to the biosensor chip,
wherein the biosensor chip comprises:
a reaction portion which is formed to be electrically connected to a plurality of sensor electrodes and to which the biological material is supplied, and
the measuring instrument comprises:
an insertion determining circuit which determines attachment and detachment of the biosensor chip;
a biological information measuring circuit which measures the biological information;
an insertion portion into which the biosensor chip can be inserted;
an insertion determining circuit side connector electrode which is electrically connected to the insertion determining circuit and is provided to come in electrical contact with a first sensor electrode of the biosensor chip when the biosensor chip is inserted into the insertion portion;
a measuring circuit side connector electrode which is electrically connected to the biological information measuring circuit and is provided to come in electrical contact with a second sensor electrode of the biosensor chip when the biosensor chip is inserted into the insertion portion; and
a ground electrode provided to come in electrical contact with the first sensor electrode when the biosensor chip is inserted into the insertion portion,
wherein the insertion determining circuit side connector electrode and the ground electrode are structured and arranged to come into the electrical contact with the first sensor electrode contemporaneously with the measuring circuit side connector electrode coming into the electrical contact with the second sensor electrode when the biosensor chip is inserted in the insertion portion, and
wherein the insertion determining circuit side connector electrode and the ground electrode are structured and arranged to remain in the electrical contact with the first sensor electrode, and the measuring circuit side connector electrode is provided to remain in the electrical contact with the second sensor electrode when the biosensor chip is fully inserted in the insertion portion and throughout the insertion from the contemporaneous electrical contact through the biosensor chip being fully inserted.

2. The biosensor system according to claim 1, wherein the sensor electrodes of the biosensor chip are formed of a sensor electrode member having an electric resistance value higher than a conductive metal.

3. The biosensor system according to claim 2, wherein the sensor electrode member is carbon.

4. The biosensor system according to claim 1, further comprising:
a voltage switching section provided between a reference voltage application section and the insertion determining circuit side connector electrode and capable of switching a voltage applied to the insertion determining circuit side connector electrode to a reference voltage or a ground potential, wherein the voltage switching section is set to perform switching from the reference voltage to the ground potential after determination on insertion of the biosensor chip by the sensor insertion determining circuit.

5. The biosensor system according to claim 1, wherein the ground electrode is used in both the insertion determining circuit and the biological information measuring circuit.

6. A measuring instrument comprising:
an insertion determining circuit which determines attachment and detachment of a biosensor chip;
a biological information measuring circuit which measures biological information;
an insertion portion into which the biosensor chip can be inserted;
an insertion determining circuit side connector electrode which is electrically connected to the insertion determining circuit and is provided to come in electrical contact with a first sensor electrode when the biosensor chip is inserted into the insertion portion;
a measuring circuit side connector electrode which is electrically connected to the biological information measuring circuit and is provided to come in electrical contact with a second sensor electrode when the biosensor chip is inserted into the insertion portion; and
a ground electrode provided to come in electrical contact with the first sensor electrode when the biosensor chip is inserted into the insertion portion,
wherein the insertion determining circuit side connector electrode and the ground electrode are structured and arranged to come into the electrical contact with the first sensor electrode contemporaneously with the measuring circuit side connector electrode coming into the electrical contact with the second sensor electrode when the biosensor chip is inserted in the insertion portion, and
wherein the insertion determining circuit side connector electrode and the ground electrode are structured and arranged to remain in the electrical contact with the first sensor electrode, and the measuring circuit side connector electrode is provided to remain in the electrical contact with the second sensor electrode when the biosensor chip is fully inserted in the insertion portion and throughout the insertion from the contemporaneous electrical contact through the biosensor chip being fully inserted.

7. The measuring instrument according to claim 6, further comprising:
a voltage switching section provided between a reference voltage application section and the insertion determining circuit side connector electrode and capable of switching a voltage applied to the insertion determining circuit side connector electrode to a reference voltage or a ground potential, wherein the voltage switching section is set to perform switching from the reference voltage to the ground potential after determination on insertion of the biosensor chip by the sensor insertion determining circuit.

8. The measuring instrument according to claim 7, wherein a pull-up resistor is provided between the reference voltage application section and the insertion determining circuit side connector electrode, and the voltage switching section is provided between the pull-up resistor and the reference voltage application section.

9. The measuring instrument according to claim 7, wherein a pull-up resistor is provided between the reference voltage application section and the insertion determining circuit side connector electrode, and the voltage switching section is provided between the pull-up resistor and the insertion determining circuit side connector electrode.

10. The measuring instrument according to claim 6, wherein the ground electrode is used in both the insertion determining circuit and the biological information measuring circuit.

11. A biosensor chip attachable to or detachable from a measuring instrument that comprises a sensor insertion determining circuit which determines attachment and detachment of the biosensor chip, a biological information measuring circuit which measures biological information, an insertion portion into which the biosensor chip can be inserted, an insertion determining circuit side connector electrode which is electrically connected to the sensor insertion determining circuit and is provided in the insertion portion, a measuring circuit side connector electrode which is electrically connected to the biological information measuring circuit and is provided in the insertion portion, and a ground electrode provided in the insertion portion, the biosensor chip comprising:
a reaction portion to which a biological material is supplied;
a first sensor electrode provided to come in contact with the insertion determining circuit side connector electrode when inserted into the insertion portion;
a second sensor electrode provided such that one end thereof comes in contact with the measuring circuit side connector electrode and the other end is electrically connected to the reaction portion when inserted into the insertion portion; and
a third sensor electrode provided such that one end thereof comes in contact with the ground electrode and the other end is electrically connected to the reaction portion when inserted into the insertion portion, wherein the first sensor electrode is electrically connected to the reaction portion through the third sensor electrode.

12. The biosensor chip according to claim 11, wherein the first sensor electrode, the second sensor electrode and the third sensor electrode are formed of a sensor electrode member having an electric resistance value higher than a conductive metal.

13. The biosensor chip according to claim 12, wherein the sensor electrode member is carbon.

14. The biosensor chip according to claim 11, wherein the ground electrode is used in both the insertion determining circuit and the biological information measuring circuit.

15. A measuring instrument comprising:
an insertion determining circuit which determines attachment and detachment of a biosensor chip;
a biological information measuring circuit which measures biological information;
an insertion portion into which the biosensor chip can be inserted;

an insertion determining circuit side connector electrode which is electrically connected to the insertion determining circuit and is provided to come in contact with a first sensor electrode when the biosensor chip is inserted into the insertion portion;

a measuring circuit side connector electrode which is electrically connected to the biological information measuring circuit and is provided to come in contact with a second sensor electrode when the biosensor chip is inserted into the insertion portion;

a ground electrode provided to come in electrical contact with the first sensor electrode when the biosensor chip is inserted into the insertion portion; and a voltage switching section capable of switching a voltage applied to the insertion determining circuit side connector electrode to a reference voltage or a ground potential, wherein the voltage switching section is set to perform switching from the reference voltage to the ground potential after determination on insertion of the biosensor chip by the sensor insertion determining circuit.

16. A measuring instrument comprising:

an insertion determining circuit which determines attachment and detachment of a biosensor chip;

a biological information measuring circuit which measures biological information;

an insertion portion into which the biosensor chip can be inserted;

an insertion determining circuit side connector electrode which is electrically connected to the insertion determining circuit and is provided to come in electrical contact with a first sensor electrode when the biosensor chip is inserted into the insertion portion;

a measuring circuit side connector electrode which is electrically connected to the biological information measuring circuit and is provided to come in electrical contact with a second sensor electrode when the biosensor chip is inserted into the insertion portion; and a ground electrode provided to come in electrical contact with the first sensor electrode when the biosensor chip is inserted into the insertion portion, wherein the insertion determining circuit side connector electrode and the ground electrode are structured and arranged to come into the electrical contact with the first sensor electrode contemporaneously with the measuring circuit side connector electrode coming into the electrical contact with the second sensor electrode when the biosensor chip is inserted in the insertion portion, and wherein the insertion determining circuit side connector electrode and the ground electrode are structured and arranged to remain in the electrical contact with the first sensor electrode, and the measuring circuit side connector electrode is provided to remain in the electrical contact with the second sensor electrode when the biosensor chip is fully inserted in the insertion portion, the measuring circuit further comprising a voltage switching section provided between a reference voltage application section and the insertion determining circuit side connector electrode and capable of switching a voltage applied to the insertion determining circuit side connector electrode to a reference voltage or a ground potential, wherein the voltage switching section is set to perform switching from the reference voltage to the ground potential after determination on insertion of the biosensor chip by the sensor insertion determining circuit.

17. The measuring instrument according to claim 16, wherein a pull-up resistor is provided between the reference voltage application section and the insertion determining circuit side connector electrode, and the voltage switching section is provided between the pull-up resistor and the reference voltage application section.

18. The measuring instrument according to claim 16, wherein a pull-up resistor is provided between the reference voltage application section and the insertion determining circuit side connector electrode, and the voltage switching section is provided between the pull-up resistor and the insertion determining circuit side connector electrode.

19. A biosensor system comprising:

a biosensor chip; and a measuring instrument which measures biological information on a biological material supplied to the biosensor chip, wherein the biosensor chip comprises:

a reaction portion which is formed to be electrically connected to a plurality of sensor electrodes and to which the biological material is supplied, and the measuring instrument comprises:

an insertion determining circuit which determines attachment and detachment of the biosensor chip;

a biological information measuring circuit which measures the biological information;

an insertion portion into which the biosensor chip can be inserted;

an insertion determining circuit side connector electrode which is electrically connected to the insertion determining circuit and is provided to come in electrical contact with a first sensor electrode of the biosensor chip when the biosensor chip is inserted into the insertion portion;

a measuring circuit side connector electrode which is electrically connected to the biological information measuring circuit and is provided to come in electrical contact with a second sensor electrode of the biosensor chip when the biosensor chip is inserted into the insertion portion; and a ground electrode provided to come in electrical contact with the first sensor electrode when the biosensor chip is inserted into the insertion portion, wherein the insertion determining circuit side connector electrode and the ground electrode are structured and arranged to come into the electrical contact with the first sensor electrode contemporaneously with the measuring circuit side connector electrode coming into the electrical contact with the second sensor electrode when the biosensor chip is inserted in the insertion portion, and wherein the insertion determining circuit side connector electrode and the ground electrode are structured and arranged to remain in the electrical contact with the first sensor electrode, and the measuring circuit side connector electrode is provided to remain in the electrical contact with the second sensor electrode when the biosensor chip is fully inserted in the insertion portion, the biosensor system further comprising a voltage switching section provided between a reference voltage application section and the insertion determining circuit side connector electrode and capable of switching a voltage applied to the insertion determining circuit side connector electrode to a reference voltage or a ground potential, wherein the voltage switching section is set to perform switching from the reference voltage to the ground potential after determination on insertion of the biosensor chip by the sensor insertion determining circuit.

20. A biosensor system comprising:
a biosensor chip; and
a measuring instrument which measures biological information on a biological material supplied to the biosensor chip,
wherein the biosensor chip comprises:
   a reaction portion which is formed to be electrically connected to a plurality of sensor electrodes and to which the biological material is supplied, and
the measuring instrument comprises:
   an insertion determining circuit which determines attachment and detachment of the biosensor chip;
   a biological information measuring circuit which measures the biological information;
   an insertion portion into which the biosensor chip can be inserted;
   an insertion determining circuit side connector electrode which is electrically connected to the insertion determining circuit and is provided to come in electrical contact with a first sensor electrode of the biosensor chip when the biosensor chip is inserted into the insertion portion;
   a measuring circuit side connector electrode which is electrically connected to the biological information measuring circuit and is provided to come in electrical contact with a second sensor electrode of the biosensor chip when the biosensor chip is inserted into the insertion portion;
   a ground electrode provided to come in electrical contact with the first sensor electrode when the biosensor chip is inserted into the insertion portion; and
   a switch provided between a reference voltage application section and the insertion determining circuit side connector electrode and operable to switch a voltage applied to the insertion determining circuit side connector electrode to a reference voltage or a ground potential,
wherein the insertion determining circuit side connector electrode and the ground electrode are structured and arranged to come into the electrical contact with the first sensor electrode contemporaneously with the measuring circuit side connector electrode coming into the electrical contact with the second sensor electrode when the biosensor chip is inserted in the insertion portion,
wherein the insertion determining circuit side connector electrode and the ground electrode are structured and arranged to remain in the electrical contact with the first sensor electrode, and the measuring circuit side connector electrode is provided to remain in the electrical contact with the second sensor electrode when the biosensor chip is fully inserted in the insertion portion, and
wherein before the biosensor chip is inserted, the switch is connected to the reference voltage application section, and when the biosensor chip is inserted, the switch is connected to the a ground potential by detecting a potential change of the sensor insertion determining circuit.

21. A measuring instrument comprising:
an insertion determining circuit which determines attachment and detachment of a biosensor chip;
a biological information measuring circuit which measures biological information;
an insertion portion into which the biosensor chip can be inserted;
an insertion determining circuit side connector electrode which is electrically connected to the insertion determining circuit and is provided to come in electrical contact with a first sensor electrode when the biosensor chip is inserted into the insertion portion;
a measuring circuit side connector electrode which is electrically connected to the biological information measuring circuit and is provided to come in electrical contact with a second sensor electrode when the biosensor chip is inserted into the insertion portion;
a ground electrode provided to come in electrical contact with the first sensor electrode when the biosensor chip is inserted into the insertion portion; and
a switch provided between a reference voltage application section and the insertion determining circuit side connector electrode and operable to switch a voltage applied to the insertion determining circuit side connector electrode to a reference voltage or a ground potential,
wherein the insertion determining circuit side connector electrode and the ground electrode are structured and arranged to come into the electrical contact with the first sensor electrode contemporaneously with the measuring circuit side connector electrode coming into the electrical contact with the second sensor electrode when the biosensor chip is inserted in the insertion portion,
wherein the insertion determining circuit side connector electrode and the ground electrode are structured and arranged to remain in the electrical contact with the first sensor electrode, and the measuring circuit side connector electrode is provided to remain in the electrical contact with the second sensor electrode when the biosensor chip is fully inserted in the insertion portion, and
wherein before the biosensor chip is inserted, the switch is connected to the reference voltage application section, and when the biosensor chip is inserted, the switch is connected to the a ground potential by detecting a potential change of the sensor insertion determining circuit.

* * * * *